United States Patent [19]

Bertenshaw et al.

[11] 4,174,334
[45] Nov. 13, 1979

[54] SURGICAL CEMENT COMPOSITIONS CONTAINING ALUMINO BORATE GLASS AND A POLYMER GLASS AND A POLYMER CONTAINING RECURRING CARBOXYLIC OR CARBOXYLATE GROUPS

[75] Inventors: Barry W. Bertenshaw; Edward C. Combe; David C. Tidy, all of Manchester; John N. C. Laycock, Runcorn, all of England

[73] Assignee: Imperial Chemical Industries Limited, London, England

[21] Appl. No.: 849,360

[22] Filed: Nov. 7, 1977

[30] Foreign Application Priority Data

Nov. 12, 1976 [GB] United Kingdom ............... 47211/76

[51] Int. Cl.$^2$ .............................................. C08L 33/00
[52] U.S. Cl. ................................ 260/29.6 M; 106/35; 260/29.6 S
[58] Field of Search ...................... 260/29.6 M, 29.6 S; 106/35

[56] References Cited

U.S. PATENT DOCUMENTS

| | | | |
|---|---|---|---|
| 3,047,408 | 7/1962 | Dougherty | 106/35 |
| 3,814,717 | 6/1974 | Wilson et al. | 260/29.6 M |
| 3,962,267 | 7/1976 | Suzuki et al. | 260/29.6 M |
| 4,016,124 | 4/1977 | Crisp et al. | 260/29.6 M |

OTHER PUBLICATIONS

Hirayama, *J. Am. Ceramic Soc.* 44, No. 12, 1961, pp. 602–606.

*Primary Examiner*—Maurice J. Welsh
*Attorney, Agent, or Firm*—Cushman, Darby & Cushman

[57] ABSTRACT

Alumino-borate glasses containing a ternary oxide an alkaline earth or alkali metal oxide are used in powdered form with an organic polycarboxylic acid (preferably polyacrylic acid) to make improved surgical cements especially useful in dentistry.

15 Claims, No Drawings

SURGICAL CEMENT COMPOSITIONS CONTAINING ALUMINO BORATE GLASS AND A POLYMER GLASS AND A POLYMER CONTAINING RECURRING CARBOXYLIC OR CARBOXYLATE GROUPS

This invention relates to cement compositions for surgical use.

It is known that cement compositions comprising an organic polymer and an inorganic filler and/or hardener may be used for surgical purposes for example as filling compositions and sealing compositions in dentistry.

Compositions comprising organic polymers containing acidic groups for example polymers of unsaturated carboxylic acids hardened with reactive basic fillers are known as surgical cements but their surface characteristics, which are important in many applications such as dentistry, are not ideal. Moreover the hardening rates of such cements are often difficult to control.

We have now found that improved surface characteristics combined with better control of the hardening rate of the cement can be obtained by using a mixed oxide glass as the filler/hardener for the organic polymer.

According to the present invention there is provided a cement composition comprising:
(i) an alumino-borate glass in powdered form containing as a ternary oxide for the glass at least one alkali metal or alkaline earth metal oxide and
(ii) a water soluble organic polymer having covalently bound to the polymer chain recurring carboxylic acid or carboxylate ion groups.

The cement composition may be mixed with an appropriate quantity of water to form a paste whereupon the paste soon begins to harden and quickly sets to a solid. The cement composition should therefore be stored in a substantially dry condition.

Accordingly the invention provides an aqueous composition comprising the components (i) and (ii) as specified above together with water. The invention also includes the hardened cement so produced.

Alternatively the water soluble organic polymer may be first dissolved in water and the polymer solution mixed with powdered glass whenever the cement is required for use.

Thus according to a further aspect of the invention there is provided a cement-forming pack comprising as constituent parts
(i) an alumino-borate glass in powdered form containing as a ternary oxide for the glass at least one alkali metal or alkaline earth metal oxide and
(ii) a solution in water of an organic polymer having covalently bound recurring carboxylic acid groups,
the two parts on mixing being capable of forming a hardening cement.

The alumino-borate glass may be prepared by fusing together glass-forming proportions of at least three oxides, aluminium oxide, boric oxide and an oxide of an alkaline earth or alkali metal. Hydrated oxides, hydroxides or carbonates may be used if they are available, and in some instances may be more convenient for example in the case of an alkali metal oxide which in anhydrous form may be too reactive to use. The proportions of the three oxides which do in fact form a glass after fusion, referred to above as "glass-forming proportions", may be determined empirically by experimentation or may be obtained by reference to phase diagrams for example those published in Journal of American Ceramic Society, 1961 Vol. 44 No. 12 pp. 602–606 by Chikara Hirayama of Westinghouse Elec. Corporation. Proportions of the oxides just outside the glass-forming regions shown on such diagrams may provide the advantages of the present invention and for the purposes of this invention any constituent may be present up to 5 mole % greater than the maximum quantity or up to 5 mole %. less than the minimum quantity defined in the above reference for glass-forming regions.

Metal ions of the ternary component of the glass are believed to be leachable in the presence of acid and capable of reacting with the carboxylic acid groups of the organic polymer thus causing the hardening of the cement. The metal ions preferred are the alkaline earth metals, magnesium, calcium, barium, strontium and zinc, and the alkali metal lithium.

The aluminium oxide, boric oxide and a source of the ternary metal oxide may be fused in a crucible or like vessel at a temperature in the range 700°–1500° C. until they become liquid and can be poured out of the crucible onto a cold surface to shock-cool the mixture to form the glass.

The glass is comminuted mechanically and/or ground, for example, in a ball-mill to a particle size of ca 100 $\mu$m preferably ca. 50 $\mu$m or less. The oversize particles are sieved out by a sieve in order to select a uniformly small grade of powdered glass particles. The degree of fineness of the powder should be such that it produces a smooth cement paste which is clinically acceptable Preferably the degree of fineness of the powdered glass is such that it passes through a 150 mesh sieve, more preferably through a 300 mesh sieve.

The concentration of alkaline earth metal or alkali metal in the glass may be varied so as to provide cements having different physical properties. In general the higher the concentration of these metals the faster the reaction with the organic polymer and the shorter the setting time of the cement. However, it is usually found that a certain minimum quantity of alkali or alkaline earth metal is necessary for glass formation in the alumino-borate ternary system. If this minimum provides too short a setting time it is usually possible to lengthen this time by increasing the proportion of aluminium to boron in the glass.

The alumino-borate compositions used in this invention may contain more than the three oxide components hereinbefore specified and advantageously other inorganic oxides may be added in addition to alkaline earth or alkali metal oxides.

Alternatively, more than one of the components specified as the ternary oxide component may be usefully added to obtain optimum properties of the glass for example, two alkaline earths or an alkali metal oxide with an alkaline earth in order to achieve a particular balance of reactivity desired and hence an optimum setting time or hardness of the cement. Examples of other oxides which may be added as a fourth type of inorganic oxide component for the glass are silicon dioxide, lead oxide and phosphorus oxides.

Quaternary components which are not oxides may also be added in minor amounts if desired, especially inorganic salts, e.g. fluorides, fluoro-silicates, phosphates, sulphates and carbonates of various metals including such metals as aluminium, calcium, barium and sodium.

The presence of quaternary components in the glass may be advantageous in contributing to the setting characteristics, the appearance or other surface properties of the final cement. Thus once an acceptable ternary composition (e.g. from standpoint of setting time and hardness) has been established, according to the invention other components may be added to improve the aesthetic appeal of the cement composition. Inert fillers, for example those conventionally used in polymeric compositions, may be used if clinically acceptable.

The covalently bound carboxylic acid or carboxylate ion groups in the organic polymer are required to be available for reaction with the basic oxides in the glass. These carboxylic groups may conveniently be present as terminal groups on long or short branches to the main polymer chain and may, if desired, be substituents of a cyclic system (either an alicyclic or aromatic system.)

Preferred polymers are those formed by polymerisation or copolymerisation of unsaturated aliphatic carboxylic acids which will thus produce sequences of poly(carboxylic acid) units in the polymer, for example, especially acrylic, methacrylic, itaconic, or fumaric acids. Particularly preferred polymers are poly(acrylic acid) and poly(methacrylic acid).

The carboxylic acid polymer is conveniently used in the form of a solution, preferably at a concentration in the range from 10 to 60%. by weight.

The molecular weight of the polymer is preferred to be from 10,000 to 200,000. Cement-forming packs in accordance with this invention preferably comprise the poly-(carboxylic acid) in the form of an aqueous solution containing from 20% to 60% by weight of the polymeric acid.

The pack may be a two part pack in which the weight ratio of powder to solution in the two parts is preferably from 0.5:1 to 5:1 so that when the entire contents of the two parts are mixed together a rapidly hardening plastic mass is obtained. The pack may contain the powder and the liquid in separate capsules or sealed sachets; the total amount of powder and of liquid in the pack being in the desired ratio. In another embodiment both components may be encapsulated in the same capsule, in separate compartments or in the same compartment provided that steps are taken to prevent premature reaction, e.g. freezing or coating the particles of the powder. In a still further embodiment the pack may be a one part pack containing an intimately blended mixture of the glass powder and solid water soluble poly(-carboxylic acid) in the ratio of 1:1 to 10:1 which can be mixed with water to produce cement.

In the above mentioned embodiments the glass powder may be usefully from 15 to 85% by weight, the poly(carboxylic acid) from 3 to 50% by weight, and the water from 5 to 70% by weight, of the total composition.

Although poly(carboxylic acids) having a relative viscosity of from 1.05 to 2.0 are readily water soluble, the choice of concentration and molecular weight should be such as to make a solution which is not too viscous since otherwise "cobwebbing" may become a problem when the desired quantity of solution is removed from its container and mixed with glass powder. For good cement formation a preferred concentration range is from 40 to 55% by weight and a preferred relative viscosity range is from 1.10 to 1.60. Particularly preferred cements may be produced using from 44 to 52% concentrations of a polyacrylic acid with a relative viscosity of from 1.20 to 1.30. It is noteworthy, when selecting suitable combinations of concentrations and molecular weight, that stronger solutions of any particular polymer are more difficult to mix but weaker solutions give lower cement strengths.

Many of the cements of this invention are designed to be made by the dental practitioner immediately prior to use on the patient in a conventional manner. The materials in the one or two part packs may be mixed together when ready for use to form a plastic mass which can be cast, moulded or otherwise formed into the required shape during the brief period in which the mixture retains its plastic properties. For example, a quantity of poly(carboxylic acid) solution sufficient to make up one small batch of cement may be easily withdrawn from its container using a dental spatula or similar instrument or extruded from a tube or like container and this may be mixed with a quantity of the glass powder on a suitable surface. The components can be mixed quite rapidly to give a uniform mass which commences to harden within a few minutes and is conveniently set within 20 minutes (preferably 10 minutes) of mixing.

In addition to the other parameters mentioned above the rate of hardening and strength of final product, are determined by the powder/liquid ratio which is preferably as high as possible compatible with adequate working time. The optimum ratio for a particular powder and liquid may be determined readily by preliminary experiments. Too little or too much powder normally results in a mixture that is more difficult to form into a desired shape. Particularly good results have been obtained with powder/liquid ratios in the range 1.5:1 to 3:1 by weight. Careful matching of the powder and liquid components will enable an acceptable plastic mass to be obtained which will harden in an acceptable time.

The materials of this invention have many applications in dentistry including use as filling materials for restoring teeth and for cementing inlays and crowns into place in the tooth, providing a base and/or lining in a tooth cavity, providing a fixing for bonds of orthodontic appliances to the teeth, sealing root-canals after endodontic treatment and for fissure-sealing.

The surgical cements of this invention may be used for all these applications in dentistry including periodontal dressings and in addition have applications in surgery for example in particular orthopaedic surgery.

The invention is illustrated by the following examples:

EXAMPLES

Appropriate weights of three or more oxides, two being boric oxide $B_2O_3$ and aluminium oxide $Al_2O_3$, were thoroughly mixed together in a platinum crucible. The crucible was heated in a muffle furnace until the oxides were fused and then the liquid contents of the crucible were poured onto a metal plate or dish to shock-cool the composition. When cold, the glass so formed was ground to a fine powder in a ball-mill and sieved down to a particle size of less than 50 $\mu$m.

An 0.2 g batch of ground glass was milled with sufficient of a viscous aqueous solution of polyacrylic acid to form a stiff paste using either a spatula and plate or an agate pestle and mortar. The solution of polyacrylic acid used was a 40% by weight solution of a polymer having a molecular weight of 30,000. (Suitable solutions are marketed for dental use under the trade name "Durelon".)

Complete mixing of the powder and solution in the paste was achieved in about 30 seconds and then hardening of the composition commenced.

The setting time of the cement was determined by observing the penetration of a standard needle as in test method No. 9 of the American Dental Association.

Portions of the cement composition were placed, soon after mixing, in a cylindrical mould of length 4 mm and diameter 2 mm and allowed to set in the mould until hard. When hard the cylindrical specimens were ejected from the mould into distilled water and were soaked for 24 hours at 37° C. prior to testing. The specimens were then tested for compressive strength on an "Instron" testing machine using a cross-head speed of 2 mm/min.

For measuring tensile strength of the set cements, specimens of length 3 mm and diameter 3 mm were prepared as described above. They were compressed diametrally on the same testing machine and at the testing speed described above. Tensile strength was calculated from the formula:

$$T.S. = \frac{2P}{\pi l d}$$

where P is the load to fracture the specimen, l is the length of the specimen and d is the diameter of the specimen.

Several samples of alumino-borate glasses were prepared containing a variety of different ternary oxides and a variety of differing glass-forming proportions as shown in the Table below. Cement compositions with aqueous polyacrylic acid were prepared from each glass as described above; measurements of setting time, tensile strength and compressive strength were conducted and the results are also presented in the Table.

The compositions when set possessed a translucent bright appearance similar to the appearance of natural dental enamel and a low solubility in water.

Translucency is important in a dental filling for good aesthetics: it is also useful to have translucent cements for luting translucent porcelain jacket crowns.

It is well known that cements containing polyacrylic acid are adhesive to tooth substance because of a chemical interaction between the carboxylate anionic groups and the calcium in the tooth substance. Since our cements contain similar chemical groups similar adhesion can be expected and in practice the compositions of this invention adhered well to dental enamel and dentine. They were observed to be superior to known compositions for a variety of applications in dentistry for example, as a cavity lining material due to their combination of high strengths after a short setting time. For example a combination made from a glass containing 49 mole % zinc oxide, 45 mole % boric oxide and 6 mole % alumina set in 5 minutes and the compressive strength at 6 minutes after mixing was observed to be as high as 10 $MN/m^2$. Such properties make the composition eminently suitable for a cavity lining on which a final filling is to be placed.

Longer setting times are preferable for applications of these surgical cements in orthopaedic surgery, for example setting times in the range from 10 minutes to 30 minutes or even one hour in order to allow the surgeon more time in which to work.

TABLE

| Glass Composition Molar % of components | | | | Properties of the Cement Composition | | |
|---|---|---|---|---|---|---|
| $B_2O_3$ | $Al_2O_3$ | Ternary oxide component | Powder/liquid ratio weight/weight | Setting Time | Compressive strength $MN/m^2$ | Tensile strength $MN/m^2$ |
| 45 | 1 | 54 ZnO | 1.5 | 45 secs | | |
| 45 | 3 | 52 ZnO | 1.5 | 2 mins | | |
| 45 | 6 | 49 ZnO | 1.5 | 7 mins | 50 | 7 |
| 45 | 6 | 49 ZnO | 1.8 | 5 mins | | |
| 50 | 17 | 33 ZnO | 1.5 | >25 mins | | |
| 45 | 15 | 40 MgO | 1.5 | >30 mins | 22 | |
| 45 | 15 | 40 MgO | 2.0 | 20 mins | | |
| 65 | 1 | 34 CaO | 1.5 | 10 mins | | |
| 65 | 6 | 29 CaO | 1.8 | 4 mins | | |
| 70 | 10 | 20 CaO | 1.5 | 15 mins | 25 | 5 |
| 65 | 13 | 22 CaO | 1.5 | >1 hr | | |
| 73 | 9 | 18 BaO | 1.5 | 12 mins | 40 | 7 |
| 66 | 5 | 29 SrO | 1.5 | <30 secs | | |
| 60 | 13 | 27 SrO | 1.5 | 4 hrs | | 8 |
| 62.5 | 10 | 27.5 SrO | 1.5 | 26 mins | 20 | 5 |
| 60 | 13 | 27 SrO | 1.8 | 3 hrs | | 9 |
| 35 | 5 | 60 $Li_2O$ | 1.5 | <30 secs | | |
| 35 | 6 | 49 ZnO + 10 PbO | 1.5 | 4 mins | | 9 |
| 42.5 | 6 | 46.5 ZnO + 5 PbO | 1.5 | <1.5 mins | | |

What we claim is:

1. A cement composition comprising:
   (i) an alumino borate glass in powdered form containing fused oxides of aluminum, boron and a third oxide type comprising at least one alkali metal or alkaline earth metal oxide and
   (ii) a water soluble organic polymer comprising a polymer chain that contains recurring carboxylic acid or carboxylate ion groups.

2. A composition as claimed in claim 1 wherein the third oxide is an oxide of magnesium, calcium, barium, strontium, zinc or lithium.

3. A composition as claimed in claim 2 wherein the alumino borate glass contains a fourth component which is an inorganic oxide or salt.

4. A composition as claimed in claim 3 wherein the fourth component is lead oxide, silica or a phosphorus oxide.

5. A composition as claimed in claim 3 wherein the third oxide is zinc oxide.

6. A composition as claimed in claim 1 wherein the alumino-borate glass powder is capable of passing through a 150 mesh sieve.

7. A composition as claimed in claim 6 wherein the powder is capable of passing through a 300 mesh sieve.

8. A composition as claimed in claim 1 wherein the organic polymer comprises a polymerised or copolymerised unsaturated carboxylic acid.

9. A composition as claimed in claim 8 wherein the polymer comprises polyacrylic acid or polymethacrylic acid.

10. A composition as claimed in claim 9 wherein the polymer is used in aqueous solution at a concentration in the range 10% to 60% by weight.

11. A composition as claimed in claim 10 wherein the weight of alumino-borate glass powder and the weight of polymer solution are in the ratio from 0.5:1 to 5:1.

12. A composition as claimed in claim 11 wherein the powder/liquid ratio is from 1.5:1 to 3:1.

13. An aqueous cement-forming composition comprising a composition as claimed in claim 1 mixed with water.

14. A cement-forming pack comprising at least the two selected parts of the composition as claimed in claim 1, the parts on mixing being capable of forming a hardening cement.

15. A dental cement, or dental filling or cavity lining material produced from a composition or cement-forming pack as claimed in claim 1.

* * * * *